United States Patent

Burkinshaw

(10) Patent No.: US 6,800,094 B2
(45) Date of Patent: Oct. 5, 2004

(54) MOBILE BEARING PATELLAR PROSTHESIS WITH ORBITAL TRANSLATION

(75) Inventor: Brian Burkinshaw, Pflugerville, TX (US)

(73) Assignee: Zimmer Technology, Inc., Chicago, IL (US)

( * ) Notice: Subject to any disclaimer, the term of this patent is extended or adjusted under 35 U.S.C. 154(b) by 11 days.

(21) Appl. No.: 10/347,971

(22) Filed: Jan. 21, 2003

(65) Prior Publication Data

US 2004/0143337 A1 Jul. 22, 2004

(51) Int. Cl.[7] .................................................. A61F 2/38
(52) U.S. Cl. ................................................. 623/20.18
(58) Field of Search ........................ 623/20.18, 20.19, 623/18.11

(56) References Cited

U.S. PATENT DOCUMENTS

| 3,972,423 A | 8/1976 | Tipton |
|---|---|---|
| 4,158,894 A | 6/1979 | Worrell |
| 4,340,978 A | 7/1982 | Buechel et al. |
| 5,609,644 A | 3/1997 | Ashby et al. |
| 5,702,465 A | 12/1997 | Burkinshaw |
| 5,871,540 A * | 2/1999 | Weissman et al. ........ 623/20.18 |
| 6,045,581 A | 4/2000 | Burkinshaw |
| 6,602,292 B2 * | 8/2003 | Burkinshaw ............... 623/20.2 |

FOREIGN PATENT DOCUMENTS

| EP | 0 582 514 A1 | 8/1993 | ............. A61F/2/38 |
|---|---|---|---|
| EP | 0 676 182 A1 | 3/1995 | ............. A61F/2/38 |

* cited by examiner

*Primary Examiner*—Kevin Shaver
*Assistant Examiner*—Michael B. Priddy
(74) *Attorney, Agent, or Firm*—Jonathan D. Feuchtwang; Zimmer Technology, Inc.

(57) ABSTRACT

A patellar prosthesis used to replace a portion of the natural knee. The patellar prosthesis comprises two basic components: A baseplate and an articulation component connected together with an attachment mechanism. This attachment mechanism provides both rotational and orbital translation such that the articulation component moves in an infinite number of directions with respect to the baseplate.

20 Claims, 2 Drawing Sheets

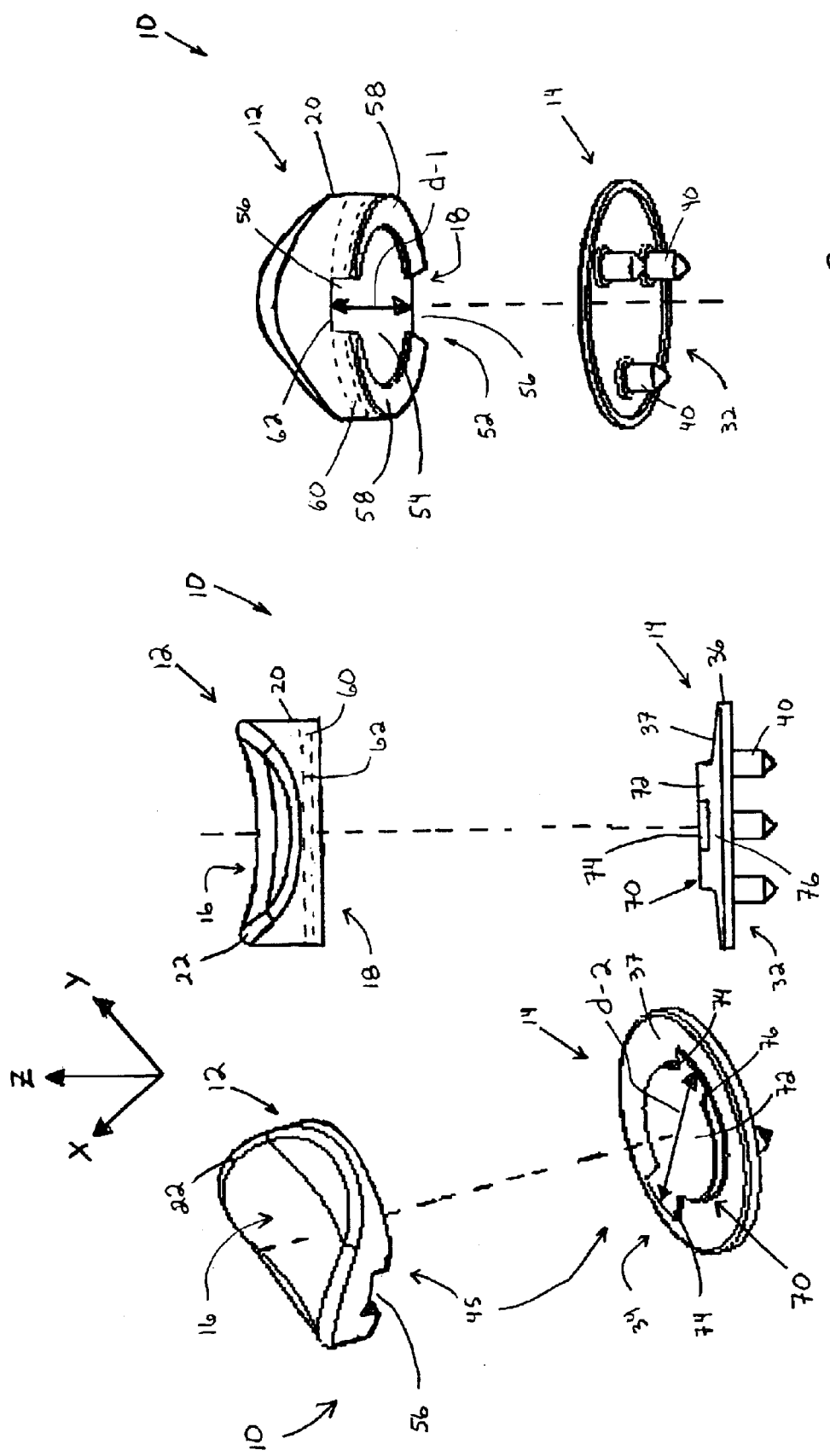

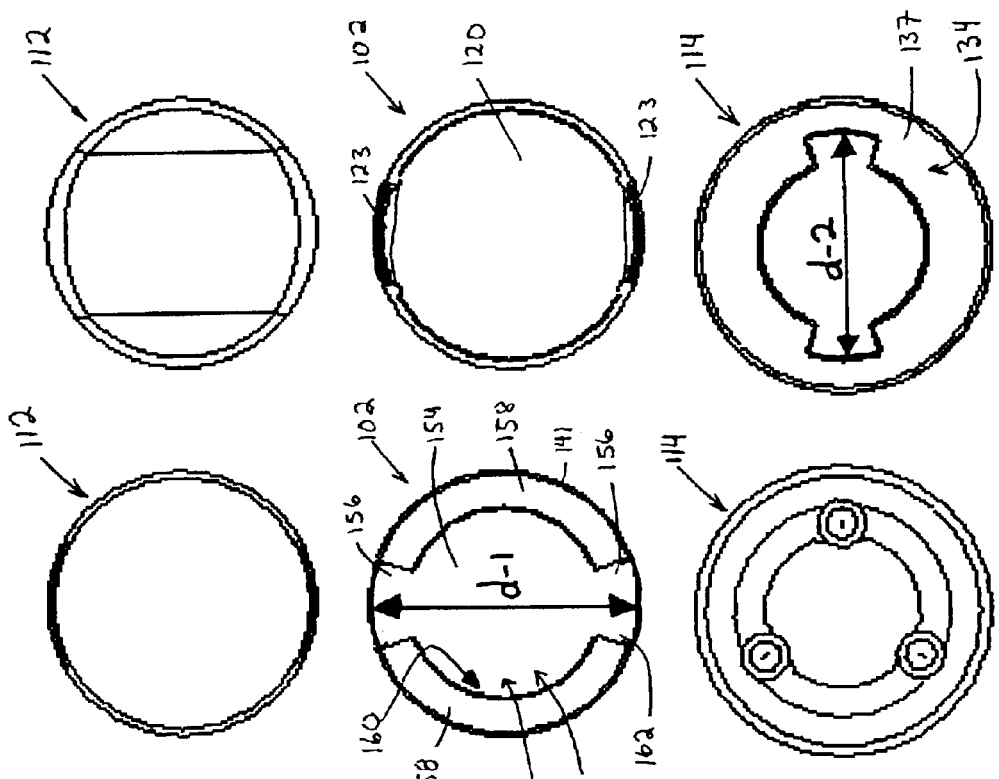
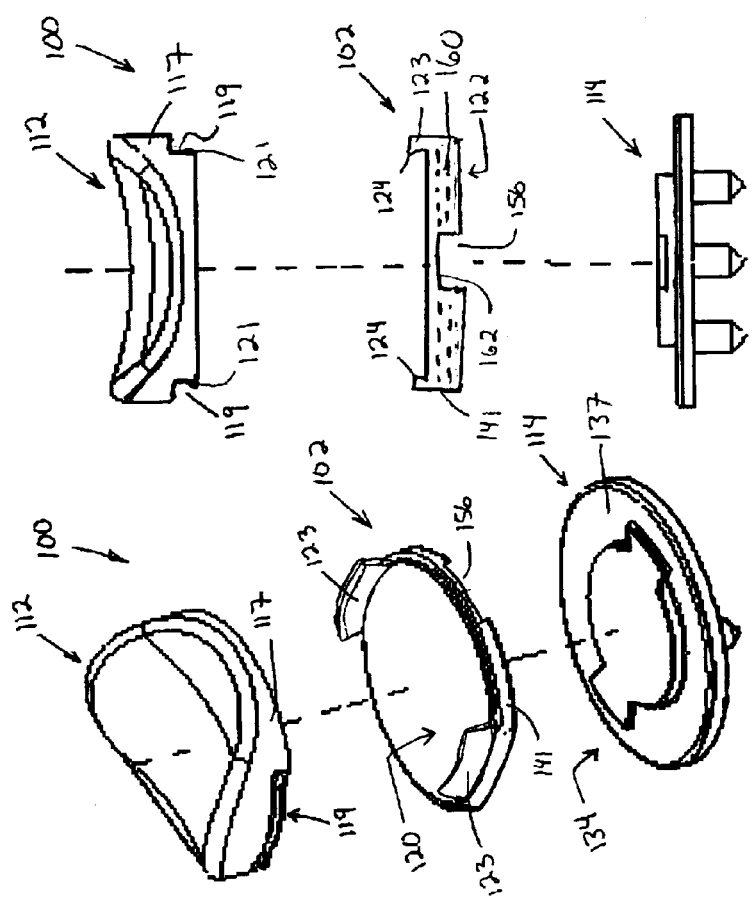
Fig. 7
Fig. 6
Fig. 5
Fig. 4

MOBILE BEARING PATELLAR PROSTHESIS WITH ORBITAL TRANSLATION

FIELD OF THE INVENTION

The present invention relates to a prosthetic patello-femoral joint assembly and, more particularly, to a mobile bearing patellar prosthesis with orbital translation such that the articulation component moves in an infinite number of directions with respect to the baseplate.

BACKGROUND OF THE INVENTION

In the United States alone, over 200,000 knee replacements are performed each year. Degenerative arthritis, or the gradual degeneration of the knee joint, is the most common reason for these replacements. In this form or arthritis, cartilage and synovium surrounding the knee wear down so underlying bones grind directly on each other.

In knee arthroplasty, portions of the natural knee joint are replaced with prosthetic components. These components include a tibial component, a femoral component, and a patellar component. The femoral component generally includes a pair of spaced condyles that articulate with the tibial component. These condyles form a trochlear groove in which the articulating surface of the patellar component moves. The components are made of materials that exhibit a low coefficient of friction when they articulate against one another.

When the articulating ends of both the femur and tibia are replaced, the procedure is referred to as total knee replacement or TKR. Much effort has been devoted to performing TKR that restores normal, pain-free functions of the knee for the lifetime of the prosthetic components.

Unfortunately, patients can experience problems with the prosthetic knee after a total knee replacement surgery. If a problem occurs, a patient may need a revision surgery wherein some or all of the prosthetic components are replaced. Historically, problems associated with the patellar prosthesis are responsible for as many as 50% of all knee implant revisions. More particularly, complications with the patello-femoral joint or patello-femoral dysfunction are the primary cause of failure in TKR.

One option in a TKR or revision surgery is to implant a prosthetic patellar component. The patellar component has a metallic back or baseplate that is permanently fixed to the patellar bone. Metal baseplates were introduced to provide a more even stress distribution on the natural patella and provide the option for either cement or cementless fixation. An articulation or bearing component is permanently connected to the baseplate to form the prosthetic patellar component. The articulation component is formed from metal or a polymer, such as ultra-high molecular weight polyethylene (UHMWPE).

Typically, the articulation component can move relative to the baseplate. This movement is extremely important to the success and proper function of the prosthetic patella. As a normal knee proceeds through a full range of flexion, the patella actually moves in several directions as it tracks along the trochlear groove. Even under normal motion, for example, the patella can move both medially and laterally, with the actual movement of the patella having a much more complicated pathway. Not surprisingly then, much effort has been devoted to designing a prosthetic patella that emulates the movement of a natural patella.

U.S. Pat. No. 5,702,465 entitled "Patella Prosthesis Having Rotational and Translational Freedom" to Burkinshaw teaches a two-piece prosthetic patella in which the articulation component moves in two different directions with respect to the baseplate. Specifically, the articulation component can rotate about the baseplate and move vertically in a longitudinal channel in the baseplate. U.S. Pat. No. 5,609,644 entitled "Prosthetic Patello Femoral Joint Assembly" to Ashby et al. teaches a two-piece prosthetic patella in which the articulation component moves in three different directions with respect to the baseplate. Specifically, the articulation component can rotate about the baseplate and move vertically in a longitudinal channel in a manner somewhat similar to U.S. Pat. No. 5,702,465. The design in Ashby, though, allows for a small amount of medial-lateral shift while the articulation component tracks along the longitudinal groove.

Despite current advances in the design of the connection between the articulation component and the baseplate, prosthetic patellae still do not fully emulate the natural movement of the patella. Specifically, these prior designs limit the movement of the articulation component with respect to the baseplate. Typically, these movements occur in straight, axial directions, such as movement down a longitudinal channel or movement in a purely medial-lateral direction while in this channel.

It, therefore, would be advantageous to provide an implantable patellar prosthesis that could closely emulate the natural movement of a patella. This prosthesis would have an articulation component that could move in an infinite number of directions with respect to the baseplate.

SUMMARY OF THE INVENTION

The present invention relates to a prosthetic patello-femoral joint assembly used to replace a portion of the natural knee and, more particularly, to a mobile bearing patellar prosthesis with orbital translation such that the articulation component moves in an infinite number of directions with respect to the baseplate. The patellar prosthesis comprises two basic components: A baseplate and an articulation component.

Each baseplate has a fixation surface and a bearing surface. The fixation surface is adapted to engage patellar bone and includes a plurality of pegs that extend outwardly from the surface to penetrate bone. The bearing surface connects to the articulation component as described herein.

Each articulation component has an articulation surface and a bearing surface. The articulation surface has a smooth contour that is adapted to articulate with a femoral component, such as a natural femur or femoral prosthesis at the patello-femoral joint. This surface may have various shapes known to those skilled in the art, such as a hyperbolic paraboloid, saddle-shape, or dome-like configuration. The bearing surface of the articulation component is adapted to engage the bearing surface of the baseplate. These surfaces are configured to lock together and then slideably contact or articulate with each other.

An attachment mechanism couples the baseplate to the articulation component so the bearing surfaces are adjacent each other. The attachment mechanism can have a variety of configurations to enable the articulation component to engage and articulate with the baseplate. In one embodiment, this mechanism includes an attachment member that protrudes from the bearing surface of the baseplate. The attachment member has a cylindrical shaft with an enlarged head. This head has a circular body portion with two wings that extend from opposite ends of the circular body. The articulation component includes a recess or keyway shaped to receive the enlarged head of the attachment member. This recess extends into the body of the articulation component and includes an undercut.

In operation, the head of the attachment member is inserted into the recess in the articulation component. The articulation component is then rotated so the wings of the head extend along the undercut. In this position, the articulation component and baseplate are engaged and locked together since the wings are captured inside the undercut.

As one important advantage of the present invention, the articulation component can move in an infinite number of directions with respect to the baseplate. Specifically, the diameter of the head of the attachment member (as measured from the ends of the wings) is less than the diameter of the bearing surface of the articulation component but greater than an inner diameter of the undercut. In other words, while the articulation component remains captured to the baseplate, the wings of the attachment member do not completely extend the full distance into the undercut. This difference in distance enables the articulation component to move while engaged and captured to the baseplate. Most importantly, the movement of the articulation component with respect to the baseplate is not limited to one or two axial directions. Instead, the articulation component can freely move in the X-Y plane in an infinite number of directions with respect to the baseplate. This movement can occur in a circular pathway along the undercuts. As such, the articulation component has "orbital translation" with respect to the baseplate.

As another advantage of the present invention, the articulation component is removeably connectable to the baseplate. In other words, even after the baseplate becomes permanently connected to the patellar bone, an articulation component can be readily attached or detached from the baseplate. During a revision surgery then, healthy bone stock of the natural patella will not be damaged or removed since the baseplate can be left attached to the patella.

As yet another advantage, the attachment mechanism of the patellar prosthesis can be utilized with various designs of articulation components and baseplates. In one embodiment, for example, the patellar prosthesis comprises only two separate or individual components: A base component and an articulation component. No other components are required to form and connect the patellar prosthesis with orbital translation. Both the articulation component and the baseplate are formed as a single unit or piece. In other words, these components are not formed from multiple pieces assembled together, but from a unitary, integral unit or piece. Further, these two components include an attachment mechanism that is integrally formed to either or both components. As such, no separate attachment mechanism is required to couple the baseplate and articulation component. In another embodiment, a third or intermediate component is used to connect the articulation component and baseplate. This third component forms the bearing surface of the articulation component and houses a portion of the attachment mechanism needed to engage with the baseplate.

Other objects and advantages of the present invention will be apparent from the following descriptions of a preferred embodiment with reference to the drawings.

BRIEF DESCRIPTION OF THE DRAWINGS

FIG. 1 is an exploded top perspective view of a two-piece patellar prosthesis of the present invention.

FIG. 2 is an exploded side view of the patellar prosthesis of FIG. 1.

FIG. 3 is an exploded bottom perspective view of the patellar prosthesis of FIG. 1.

FIG. 4 is an exploded top perspective view of a three-piece patellar prosthesis of the present invention.

FIG. 5 is an exploded side view of the patellar prosthesis of FIG. 4.

FIG. 6 is a bottom view of each component of the three-piece patellar prosthesis of FIG. 4.

FIG. 7 is a top view of each component of the three-piece patellar prosthesis of FIG. 4.

DETAILED DESCRIPTION OF THE PREFERRED EMBODIMENT

FIGS. 1–3 show a prosthetic patello-femoral joint assembly or mobile bearing patellar prosthesis 10 used to replace a portion of the natural knee. The patellar prosthesis comprises two basic components: An articulation component 12 and a baseplate 14.

The articulation component and baseplate are shown relative to mutually orthogonal reference axes X, Y and Z (FIG. 1). When a prosthesis is implanted, reference axes X, Y and Z correspond, generally, to well known and accepted anatomical directional terms. The X axis extends generally in the medial-lateral direction, the Y axis extends generally in the inferior-superior direction, and the Z axis extends generally in the posterior-anterior direction. If the prosthesis were implanted on the left patella of a human patient, the ends of each of the X, Y, and Z axes marked with an arrowhead would point generally in the medial, superior, and posterior directions, respectively. Further, the X and Y axes together form an X-Y plane.

The present invention may be utilized in various surgical techniques known to those skilled in the art. As an example, during a TKR surgery, the patella is resected in a plane generally perpendicular to the anterior-posterior direction to remove a posterior portion of the patellar bone, leaving a resected planar bony surface. When a prosthesis is implanted, the Z axis lies perpendicular to the resected planar bony surface of a patella, and the X and Y axes lie parallel to the resected planar bony surface.

Articulation component 12 is constructed of a biocompatible material having desirable wear and bearing friction properties, such as biocompatible metals and ultra-high molecular weight polyethylene (UHMWPE). Examples of suitable materials are Metasul® and Durasul® articulation components manufactured by Centerpulse Orthopedics Inc. of Austin, Tex.

Articulation component 12 includes two primary surfaces: An articulation surface 16 and a planar bearing surface 18 oppositely disposed from the articulation surface. The bearing surface 18 is generally perpendicular to the Z axis and spaced from the articulation surface 16 to define a thickness. A wall 20 extends around the outer perimeter of the articulation component and generally has an elliptical or round shape.

Articulation surface 16, in the preferred embodiment shown, is a hyperbolic paraboloid, also known as a "saddle" shape, in which the intersection of the surface 16 and wall 20 defines an undulating edge 22. Articulation surface 16, so configured, ideally provides congruent sliding contact over an extensive range of articulation between articulation component 12 and the patellar articulation surface of a femoral component, such as the natural femur or a femoral prosthetic component at the patello-femoral joint.

Baseplate 14 is constructed of a biocompatible material having desirable wear, bearing friction, and bone engaging properties that are known to those skilled in the art. Examples of such a material are UHMWPE, titanium, titanium alloys, ceramics, aluminum oxide ceramics, and cobalt chromium alloys.

Baseplate 14 includes a fixation surface 32 for engaging patellar bone, a planar bearing surface 34 generally perpendicular to the Z axis and spaced from the fixation surface 32, and an outer wall 36 that extends around the perimeter and is generally parallel to the Z axis. The baseplate generally has an elliptical or round shape to match the size and shape of the articulation component 12. Bearing surface includes a convex surface portion 37 that extends around with a ring shape.

Fixation surface 32 includes a generally planar surface portion 38 adapted to engage resected planar bony surface 13 generally parallel thereto. The surface portion 38 can be adapted to directly engage and integrate with the patellar bone with or without bone cement. Planar surface portion 38, for example, can include surface texturing to promote osseointegration of baseplate 14. A coating of hydroxyapatite, ceramic, or porous metal are examples of surface texturing known to those skilled in the art. Such coatings can be applied with plasma spraying or sintering techniques. Suitable metals for sintering include titanium and its alloys and cobalt chromium alloys. Other materials and methods for providing a surface that favors osseointegration are well known in the art.

Fixation surface 32 also includes a plurality of pins or pegs 40 that extend downward from the surface. These pegs are evenly and symmetrically spaced apart and are integrally connected to fixation surface 32. The pegs 40 are sized and shaped to be received in correspondingly shaped bores (not shown) in the patella. Specifically, each peg has a cylindrical body portion with a tapered or conical distal end. One skilled in the art will appreciate that the pegs can have various configurations and textures, such as a straight, ribbed, or tapered shape with macro-textured surface to enhance fixation with bone cement or osseointegration.

The articulation component 12 is removeably connectable to the baseplate 14. Even after the baseplate becomes permanently connected to the patellar bone, an articulation component can be readily or easily attached and detached from the baseplate. The removeable or detachable connection between the baseplate and articulation component provides a modular patellar prosthesis.

A coupling or attachment mechanism 45 located on the bearings surfaces of both components enables the articulation component 12 and baseplate 14 to be connectable to and removeable from each other.

On the bearing surface 18 of the articulation component, the attachment mechanism includes a keyway or recess 52 having a circular or elliptical center portion 54 with two rectangular slots 56 oppositely disposed from each other. Recess 52 does not cover the entire surface, but leaves two outer or bottom walls 58. These walls have a concave angulation to exactly match the convex angulation of the convex surface portion 37 on the bearing surface 34 of the baseplate 14. Further, these walls form an undercut 60 with bottom wall 62. This undercut is circular and extends around the periphery of articulation component 12 and adjacent to outer wall 20.

On the bearing surface 34 of the baseplate 14, the attachment mechanism includes an attachment member 70. This attachment mechanism has a disc-shaped body 72 with a pair of oppositely disposed, rectangular wings 74. These wings extend outwardly from the disc-shaped body and form an undercut 76 beneath themselves.

It should be noted that body 72 may have a circular or elliptical shape. An elliptical shape provides a controlled amount of orbital translation as the articulation component moves relative to the baseplate.

In order to engage or connect the articulation component 12 to the baseplate 14, attachment member 70 is positioned into recess 52 such that disc-shaped body 72 and wings 74 fit into center portion 54 and slots 56, respectively. The articulation component is then rotated in a clockwise or counterclockwise direction to lock the articulation component to the baseplate. Once locked together, the wings 74 can freely rotate along and inside the undercut 60. Walls 58 prevent the wings from disengaging from the undercut and, thus, prevent the articulation component from disengaging with the baseplate.

In order to remove the articulation component 12 from the baseplate 14, the articulation component is rotated so wings 74 of attachment member 30 are positioned in slots 56 of recess 52. The articulation component is then pulled or removed from the baseplate.

One skilled in the art will appreciate that attachment mechanism can be altered without departing from the scope of the invention. As an example, the coupling components on the articulation component and baseplate can be switched: The articulation component could be configured to have a protruding attachment member while the baseplate has a matching recess adapted to receive, engage, and lock with the attachment member. Other embodiments as well are within the scope of the invention, and FIGS. 4–7 show one such embodiment.

FIGS. 4–7 show a patellar prosthesis 100 configured similarly to the patellar prosthesis 10 of FIGS. 1–3, with several differences. The attachment mechanism is formed, in part, using a third component 102 separate and distinct from the articulation component 112 and baseplate 114. As another difference, the bearing surface 134 of baseplate 114 has a concave surface portion 137 (shown as a convex surface portion 37 in FIGS. 1 and 2). As yet another difference, the articulation component 112 includes a peripheral surface 117 with two rectangular recesses 119 that extend into surface 117 and partially around the periphery. These recesses include a lip or shoulder 121.

Component 102 includes a top surface 120 and a bottom surface 122. Two wings 123 extend upwardly from top surface 120. These wings are oppositely disposed and have a curved, rectangular shape. A lip or shoulder 124 is provided at a distal end of each wing.

The bottom surface 122 includes a keyway or recess 152 having a circular or elliptical center portion 154 with two rectangular or winged slots 156 oppositely disposed from each other. Recess 152 does not cover the entire surface, but leaves two outer or bottom walls 158. These walls have a convex angulation to exactly match a concave angulation of the concave surface portion 137 of on the bearing surface 134 of the baseplate 114. Further, these walls form an undercut 160 with bottom wall 162. This undercut is circular and extends around the periphery of third component 102 and adjacent to outer wall 141.

In order to connect the third component 102 to the articulation component 112, the top surface 120 is pushed against the underside of the articulation component until the wings 123 extend into recesses 119. As the wings are pushed upwardly, they expand radially and the shoulders 124 snap over lips 121 to lockingly engage the third component 102 to the articulation component 112. Once connected, the bottom surface 122 of the third component now becomes the bearing surface of the articulation component 112. The attachment between these two components can be designed to be non-removeable (i.e., permanent) or removeable.

Once the third component 102 is connected to the articulation component 112, the articulation component and baseplate connect, engage, and disengage in a manner similar to the articulation component 12 and baseplate 14 described in connection with FIGS. 1–3.

One important advantage of the present invention is that the articulation component can move in an infinite number of directions in the X-Y plane (FIG. 1) with respect to the baseplate. Reference should be made to the figures. Specifically, the diameter "d-2" (FIG. 1) of the top surface of the disc-shaped body 72 of attachment member 70 (as measured from the ends of the wings 74) Is less than the diameter "d-1" FIG. 3 of the bearing surface 18 of the articulation component 12. In other words, while the articulation component remains captured to the baseplate, the wings 74 of the attachment member 70 do not completely extend the full distance into the undercuts 60. This difference in distance enables the articulation component to move while engaged and captured to the baseplate. The amount of movement is equal to "d-1" minus "d-2." Most importantly, the movement of the articulation component with respect to the baseplate is not limited to one or two axial directions. Instead, the articulation component can move in the X-Y plane (FIG. 1) in an unlimited or infinite number of directions with respect to the baseplate. In other words, the articulation component can move along the X axis (i.e. in both the medial and lateral directions), along the Y axis (i.e., in both the inferior and superior directions), and along all directions within the X-Y plane (including directions that are not parallel with the X and Y axes). This movement can occur in a circular pathway along the undercuts 60 formed in the articulation component. As such, the articulation component has "orbital translation" with respect to the baseplate. It is important to note that this orbital translation is different than rotational translation. While the articulation component 12 is connected to the baseplate 14, the articulation component can rotate about the attachment member 70. This rotation occurs around the Z-axis (FIG. 1) and is in addition to the orbital translation in the X- Y plane.

It should be noted that "d–1" defines the major diameter of the bearing surface of the articulation component. Even though the length "d–1" is greater than "d–2," the articulation component cannot disengage from the baseplate until the wings 74 are aligned in the recesses 56. Specifically, walls 58 form an inner diameter that is greater than "d–2." As such, these walls 58 keep the wings engaged in the undercuts 60. The length of "d–2" should be designed to be greater than the inner diameter but less than the outer diameter of the bearing surface of the articulation component.

When the articulation component is connected to the baseplate, the bearing surfaces of each component lie in direct engagement with each other. These surfaces can slideably engage or articulate in a rotational manner about the Z-axis and in an orbital translation or infinite number of directions in the X-Y plane.

This orbital translation works equally well with the embodiment shown in FIGS. 4–7. FIGS. 6 and 7 illustrate the diameters "d–1" and "d–2" as discussed in connection with FIGS. 1–3.

As another advantage of the present invention, the bearings surfaces of the articulation component and baseplate have mating convex and concave surfaces. Specifically, FIGS. 1–3 show bearing surface 34 with a convex surface portion 37 and bearing surface 18 with a concave wall 58; and FIGS. 4–7 show a concave surface portion 137 on baseplate 114 and convex walls 158 on articulation component 112. These surfaces enable the patellar prosthesis to more closely emulate the natural movement of the patella as the articulation component slideably engages the baseplate.

Although illustrative embodiments have been shown and described, a wide range of modifications, changes, and substitutions is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A patellar prosthesis, comprising:
   a baseplate having a fixation surface adapted to engage a natural patella;
   an articulation component having an articulation surface adapted to articulate with a femoral component at a patello-femoral joint; and
   the articulation component and baseplate being connectable to the natural patella wherein the articulation component can slideably rotate about the baseplate and freely move in all directions in a plane defined by medial-lateral and inferior-superior directions independent of its rotation about the baseplate.

2. The patellar prosthesis of claim 1 wherein the articulation component and baseplate engage each other along a convex surface.

3. The patellar prosthesis of claim 1 wherein the baseplate engages the articulation component along a circular recess.

4. The patellar prosthesis of claim 3 wherein the baseplate freely moves in an infinite number of directions in the circular recess.

5. The patellar prosthesis of claim 4 wherein the baseplate includes a protrusion that engages the circular recess.

6. A two-piece patellar prosthesis adapted to replace a portion of a natural patella, the patellar prosthesis comprising:
   a baseplate having a fixation surface adapted to engage the natural patella;
   an articulation component having an articulation surface adapted to articulate with a femoral component at a patello-femoral joint and being connected to the baseplate; and
   the articulation component and baseplate being connectable to the natural patella wherein the articulation component can move in at least four different directions, including rotation about a posterior-anterior direction and including movement along a medial-lateral direction, movement along an inferior-superior direction, and movement along a plane defined by the medial-lateral and inferior-superior directions independent of its rotation about the posterior-anterior direction.

7. The patellar prosthesis of claim 6 wherein the baseplate is permanently connectable to the natural patella.

8. The patellar prosthesis of claim 7 wherein the articulation component is removeable from the baseplate.

9. The patellar prosthesis of claim 7 wherein the baseplate includes a convex surface adapted to slideably articulate with the articulation component.

10. The patellar prosthesis of claim 7 wherein the baseplate includes an attachment member, and the articulation component includes a recess adapted to engage the attachment member.

11. The patellar prosthesis of claim 10 wherein the recess includes an undercut, and the attachment member slideably moves in the undercut.

12. The patellur prosthesis of claim 9 wherein the recess is circular.

13. A patellar prosthesis adapted to replace a portion of a natural patella, the patellar prosthesis comprising:
   a baseplate having a fixation surface adapted to engage the natural patella and a bearing surface oppositely disposed from the fixation surface;
   an articulation component having an articulation surface adapted to articulate with a femoral component at a patello-femoral joint and a bearing surface adapted to slideably articulate with the bearing surface of the baseplate;
   the articulation component and baseplate being connectable to the natural patella with an X axis extending in a medial-lateral direction, a Y axis extending in an inferior-superior direction, a Z axis extending in a posterior-anterior direction, and the X and Y axes forming an X-Y plane; and
   the articulation component being rotateable about the Z axis and being moveable along the X axis, moveable along the Y axis, and moveable along multiple other directions in the X-Y plane independent of its rotation about the Z axis while the articulation component is connected to the baseplate.

14. The patellar prosthesis of claim 13 wherein the articulation component can move in an infinite number of directions in the X-Y plane while connected to the baseplate.

15. The patallar prosthesis of claim 14 wherein the articulation component and baseplate are attachable and detachable from each other.

16. The patellar prosthesis of claim 13 wherein an attachment mechanism connects the articulation component and the baseplate together, and the attachment mechanism includes a male protrusion and a female recess.

17. The patellar prosthesis of claim 16 wherein the male protrusion has a non-circular shape, and the recess includes a keyway adapted to receive the male protrusion.

18. The patellar prosthesis of claim 17 wherein the male protrusion extends outwardly from the baseplate and includes a circular body with at least one wing.

19. The patellar prosthesis of 18 wherein the female recess includes an undercut adapted to receive the wing.

20. The patellar prosthesis of claim 19 wherein the female recess includes two separate undercuts, and the circular body includes two separate wings.

* * * * *